United States Patent [19]

Vanolo et al.

[11] Patent Number: 5,383,406
[45] Date of Patent: Jan. 24, 1995

[54] BODY STRUCTURE FOR RAILWAY VEHICLES

[75] Inventors: Pietro Vanolo; Alberto Magnani, both of Torino; Emilio Debbia, Savigliano; Claudio Gugliesi, Torino; Luigi Cencio; Luciano Gerbaudo, both of Savigliano, all of Italy

[73] Assignee: Fiat Ferroviaria S.p.A., Torino, Italy

[21] Appl. No.: 94,979

[22] Filed: Jul. 23, 1993

[30] Foreign Application Priority Data

Dec. 29, 1992 [IT] Italy .................. TO92 A 001054

[51] Int. Cl.6 ............................................ B61D 17/00
[52] U.S. Cl. ................................... 105/401; 105/397; 105/422
[58] Field of Search ............... 105/396, 397, 400, 401, 105/423, 422

[56] References Cited

U.S. PATENT DOCUMENTS

| 4,974,900 | 12/1990 | Destefani et al. | 105/401 |
| 4,993,329 | 2/1991 | Takeich et al. | 105/401 |
| 5,042,395 | 8/1991 | Wackerle et al. | 105/401 |

FOREIGN PATENT DOCUMENTS

| 0354436 | 2/1990 | European Pat. Off. | 105/397 |
| 0544498 | 6/1993 | European Pat. Off. | 105/401 |
| 594309 | 9/1925 | France . | |
| 2635064 | 9/1990 | France . | |
| 1580992 | 12/1970 | Germany . | |
| 2031546 | 9/1971 | Germany . | |

OTHER PUBLICATIONS

Zev Zeitschrift Fur Eisenbahnwesen Und Verhehrstechnik, vol. 114, No. 3, Mar. 1990, Berline, Germany, pp. 87–93, G. Reif et al. "Konstruktion, Analyse und Produktion von Schurzenklappen fur Hochgeschwindigkeitszuge".

Revue Generale Des Chemins De Fer, vol. 110, No. 7/8, Jul. 1991, Paris, France, pp. 19–26, H. Lagneau et al. "Les Structures Des Vehicules".

Zeitschr. Fur Eisenbahwesen Und Verkehrstechnik--Die Eisenbahntechnik-Glasers Annalen, vol. 116, No. 11, Nov. 1992, Berlin, Germany, pp. 452–456, O. Elsner et al. "Neue Elektrische Und Dieseltriebzuge In Aluminium-Grossstrangpressprofil-Bauweise Fur Grossbritannien".

*Primary Examiner*—Mark T. Le
*Attorney, Agent, or Firm*—Sughrue, Mion, Zinn, Macpeak & Seas

[57] ABSTRACT

Body structure (1) for railway vehicles comprising a load bearing body-work defining the platform (2), the body sides (3) and the roof (4) of the body, constituted by an annular series of hollow structural panels (11, 12, 13), substantially continuous and having a length substantially corresponding to that of the body. Each structural panel (11, 12, 13) is formed by an inner wall (14) and by an outer wall (15) connected therebetween by intermediate baffles (17) having a substantially corrugated disposition with parallel generating lines (16). The longitudinal edges of each structural panel (11, 12, 13) are rigidly connected to the corresponding longitudinal edges of the adjacent panels by continuous welding.

8 Claims, 6 Drawing Sheets

BODY STRUCTURE FOR RAILWAY VEHICLES

BACKGROUND OF THE INVENTION

The present invention is related to body structures for railway vehicles, comprising a load bearing body-work defining the platform, the body sides and the roof of the body.

Traditionally such load bearing body-work is constituted by frames formed by longitudinal and transverse members, or vertical elements in the case of the body sides, to which flat or corrugated metal sheets are secured, which are fixed to the respective frames by means of solderings usually made by hand.

These conventional structures are complex from the point of view of manufacturing, require a massive intervention of skilled labor for their assembling, have vibration modes corresponding to a plurality of components having different rigidity, and moreover the frameworks employed therein are binding for the spaces with a huge conditioning of the equipments and fittings onboard the vehicle.

SUMMARY OF THE INVENTION

The object of the present invention is to provide a body structure for railway vehicle adapted to be manufactured and assembled more easily and, in particular, by the aid of automatic apparatuses, and moreover affected by very few significant vibration modes and enabling a liberty of disposition and mounting of the equipments and fittings equivalent to that of a self-bearing tube having smooth walls.

According to the invention, this object is achieved by virtue of a body structure for railway vehicles of the type set forth at the beginning, the main feature of which resides in that it is constituted by an annular series of hollow structural panels, substantially continuous and having a length substantially corresponding to that of the body, each of the said panels having respective longitudinal edges and being formed by an inner wall, an outer wall and intermediate longitudinal baffles, having a substantially corrugated disposition with generating lines parallel to one another, connecting the said inner and outer walls to each other, the longitudinal edges of each structural panel being rigidly connected to the corresponding longitudinal edges of the adjacent structural panels so as to define a tubular body, and further comprising inner transverse structural members for stabilizing the said tubular body.

By the term "structural" it is intended in the present specification that each of the said panels is adapted to bear the loads and the other operating or testing stresses of the railway vehicle.

By the term "corrugated" it is intended to designate the inner configuration of the panels, i.e. that defined by the baffles, having parallel generating lines and connecting the two walls to each other, the function of which is substantially that of stabilizing such walls.

Each structural panel can be made by metal materials or by reinforced plastic materials (structural composite materials).

In the first case each structural panel is conveniently formed by extrusion, and in the second case by means of poltrusion, which enables manufacturing each panel by a single operation forming the said corrugated intermediate baffles integrally with the respective inner and outer walls.

According to an alternative embodiment the intermediate baffles can be formed by a plate previously corrugated or bent and then rigidly fixed, by means of welding or glueing, firstly to one and then to the other of the said inner and outer walls.

The main advantages deriving from the body structure according to the invention are summarized in the following:

- rigid and uniform structure, i.e. having relatively high frequencies in the main vibration modes and reduced dispersion in the local vibrating modes;
- minimum use of material for resisting to the pressure blows due, during travel of the vehicle, to crossing with other railway vehicles and to the tunnels;
- minimum obliged distribution of the spaces, i.e. maximum versatility in the disposition of equipments and fittings within the body;
- structure adapted to be easily produced, mainly by longitudinal continuous and automated connections.

According to further aspects of the invention, the body structure can be integrated by complementary structures for localized functions and stresses (headstock girders and frameworks, supporting beams onto the bogies, stabilizing bulkheads of the cross sections, reinforcements of the access door openings), which can be conveniently formed according to the same structural-panel disposition.

Moreover the interspace of the said corrugated structural panels can be adavantageously filled with foamed materials, so as to obtain a stabilizing effect of the intermediate baffles and of the inner and outer walls, which enables manufacturing thereof with a reduced thickness of high-resistance materials, providing at the same time thermal-acoustical insulating functions.

BRIEF DESCRIPTION OF THE DRAWINGS

The invention will now be disclosed in detail with reference to the annexed drawings, provided purely by way of non limiting example, wherein.

DETAILED DESCRIPTION OF THE INVENTION

Figure 1:
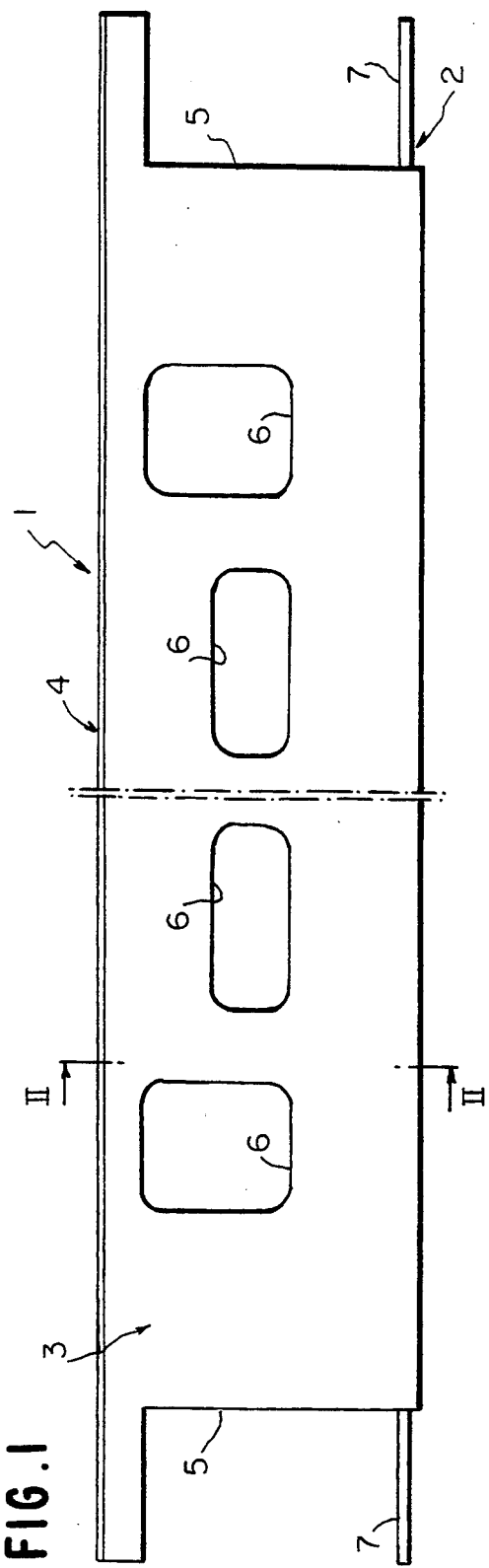
FIG. 1 is a diagrammatic lateral elevation view of a body structure for railway vehicles according to the invention.
Figure 3:
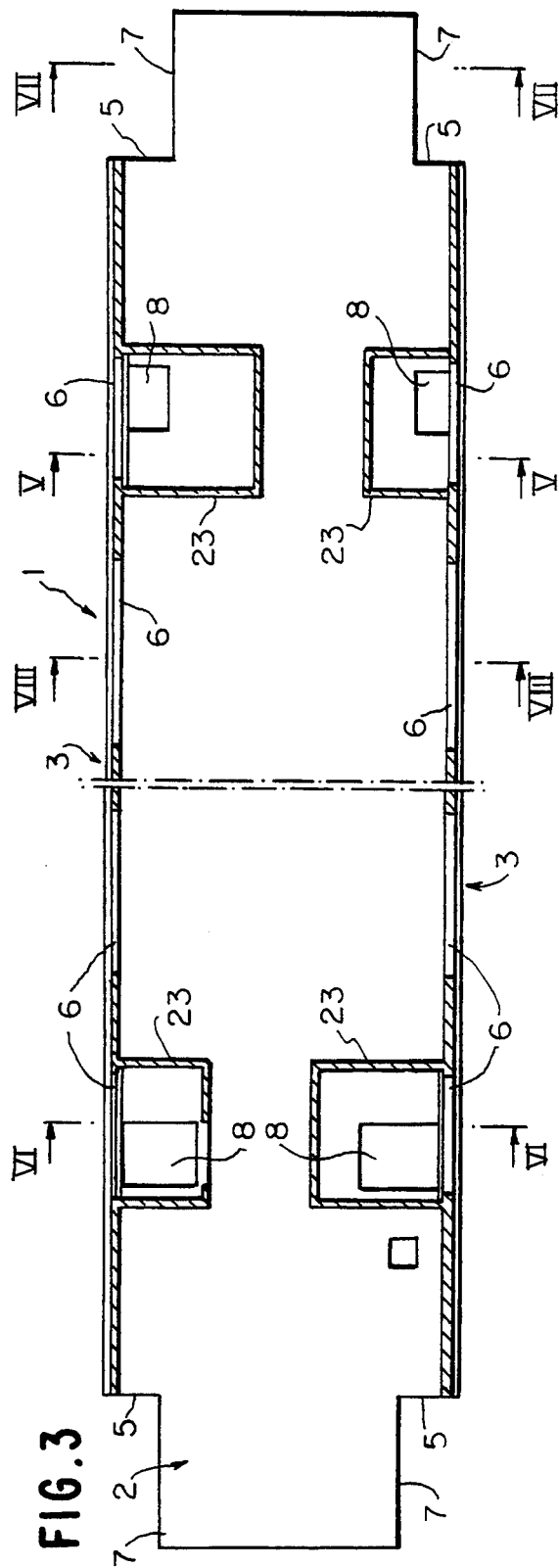
FIG. 3 is a longitudinal section in a reduced scale along line III—III of FIG. 2.

Referring to the drawings, reference numeral 1 generally indicates a body structure for railway vehicles, constituted by a load bearing tubular bodywork defining the platform 2, the body sides 3 and the roof 4 of the body.

The body sides 3 are partially interrupted in correspondence of the ends of the structure 1 so as to define two pairs of openings 5 for the access doors to the carriage, and are further formed with apertures 6 for the application of windowpanes.

The platform 2 is formed in correspondence of the door openings 5 with respective recesses 7 and is further provided, in correspondence of the areas designed to be supported by the vehicle bogies, with passages 8 for possible actuators controlling swinging motion of the body, as well as with a support trelliswork of a pantograph trolley for electric feeding, if any, in the case of a motorized vehicle.

The roof 4 is also formed with passages 10 for the support trelliswork of the pantograph trolley, if any. According to the invention the platform 2, the body sides 3 and the roof 4 are constituted by a plurality of substantially continuous (but for in the areas corresponding to the respective openings 6, 8, 10) hollow structural panels having a length corresponding to that of the body 1, provided with a substantially corrugated inner configuration and having the respective longitudinal edges rigidly connected to the corresponding longitudinal edges of the adjacent panels.

Figure 4:
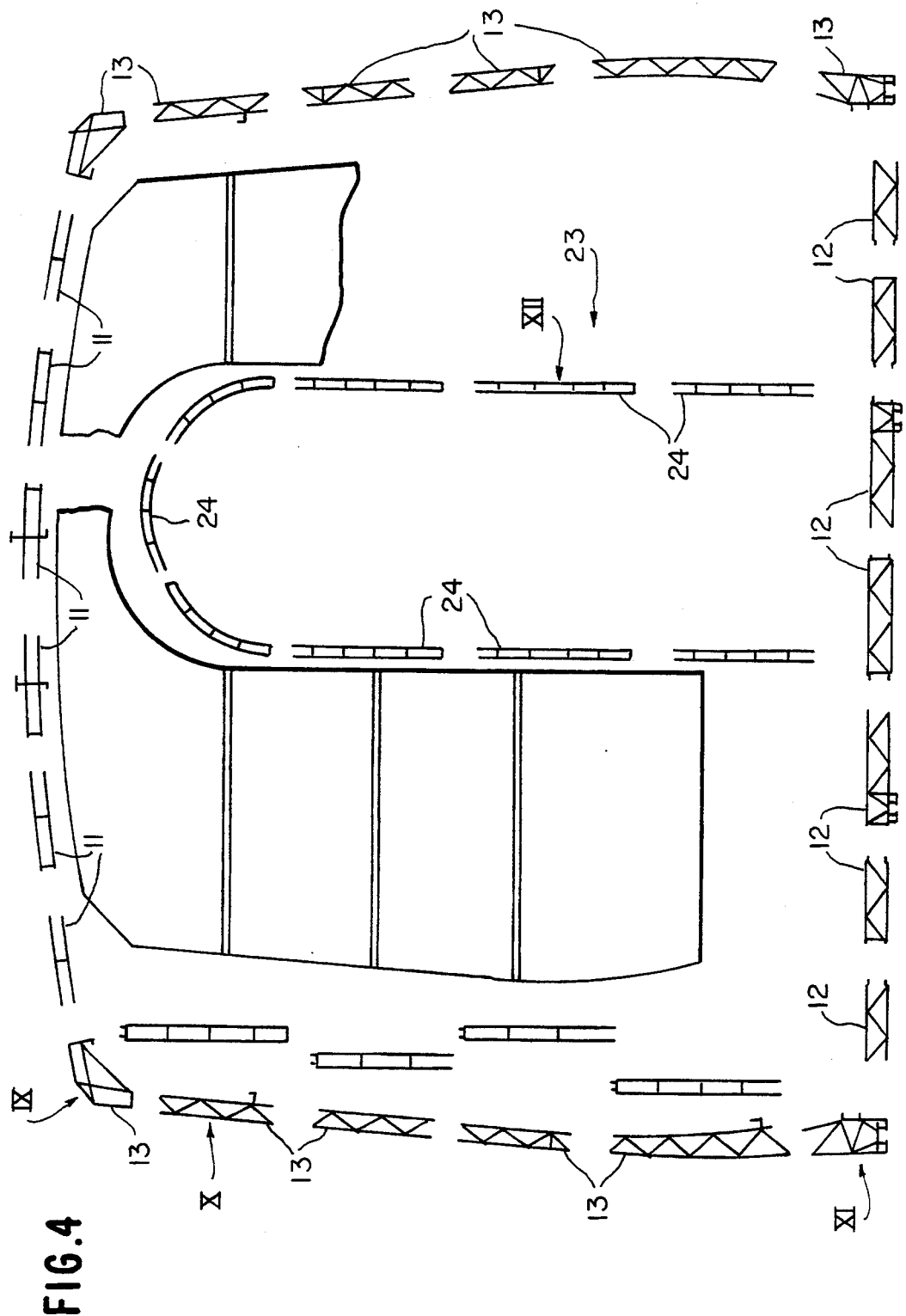
FIG. 4 shows the section of FIG. 2 before assembling of the body structure.
Figure 5:
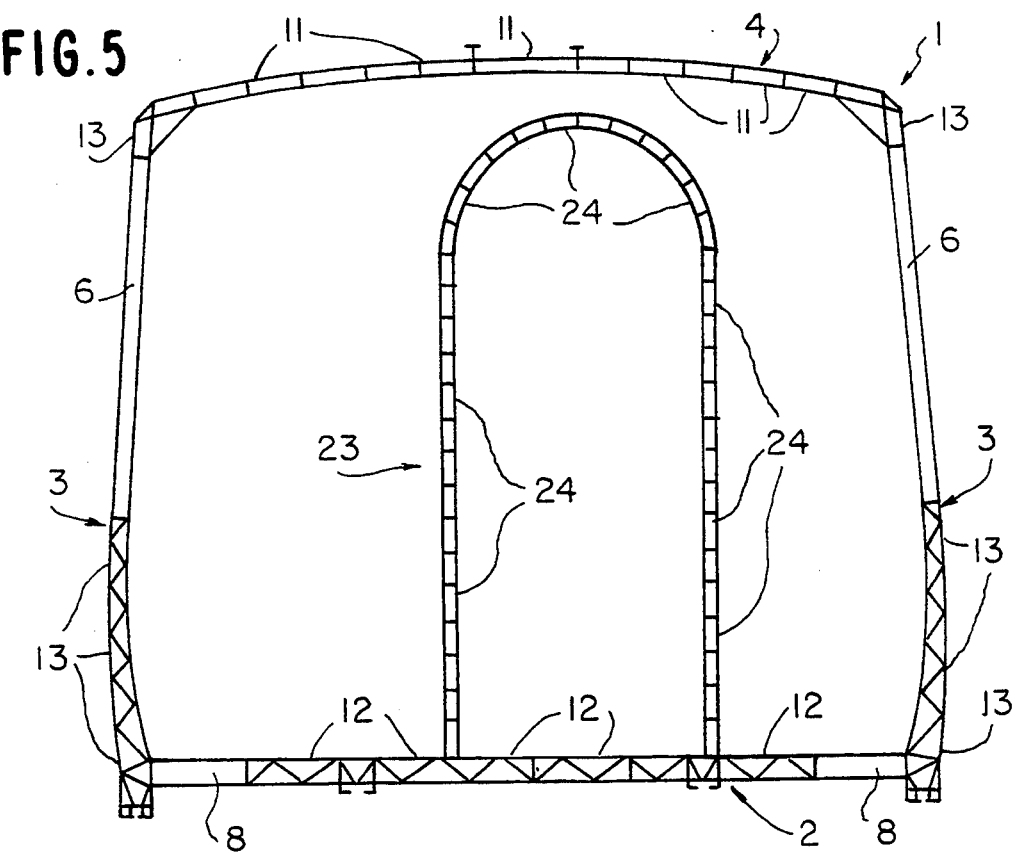
FIG. 5 is a cross section in enlarged scale along line V—V of FIG. 3.
Figure 6:
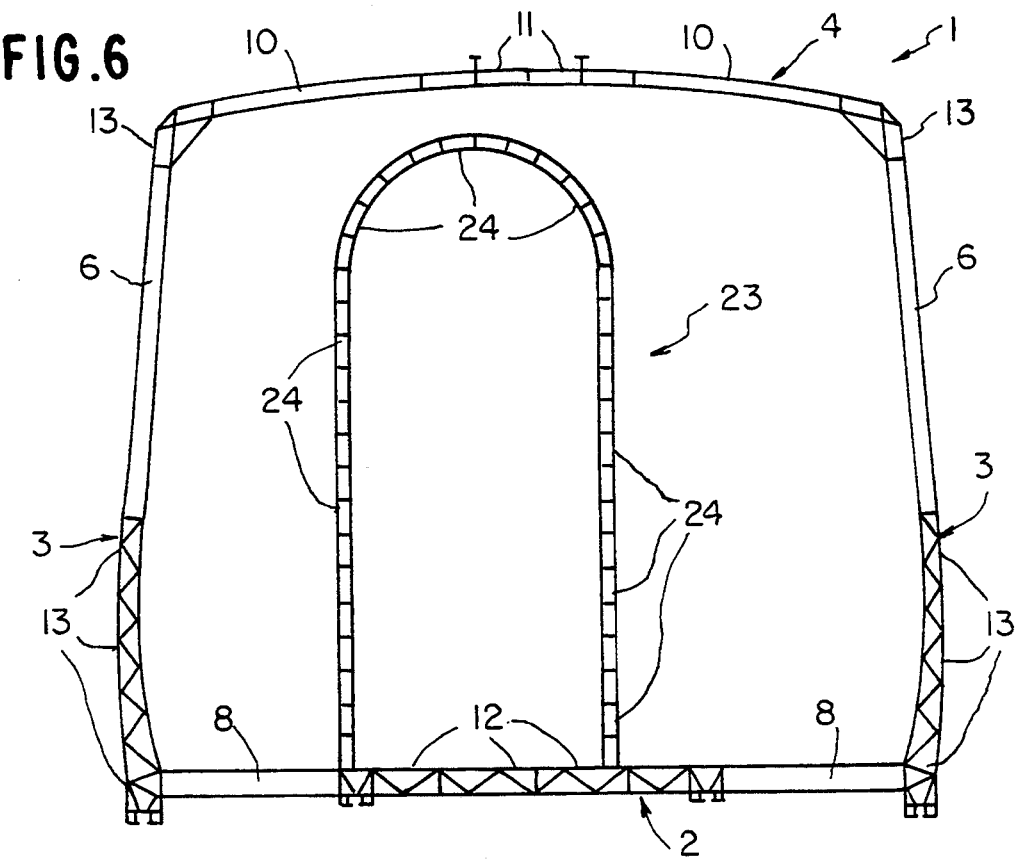
FIG. 6 is a cross section in an enlarged scale along line VI—VI of FIG. 3.
Figure 7:
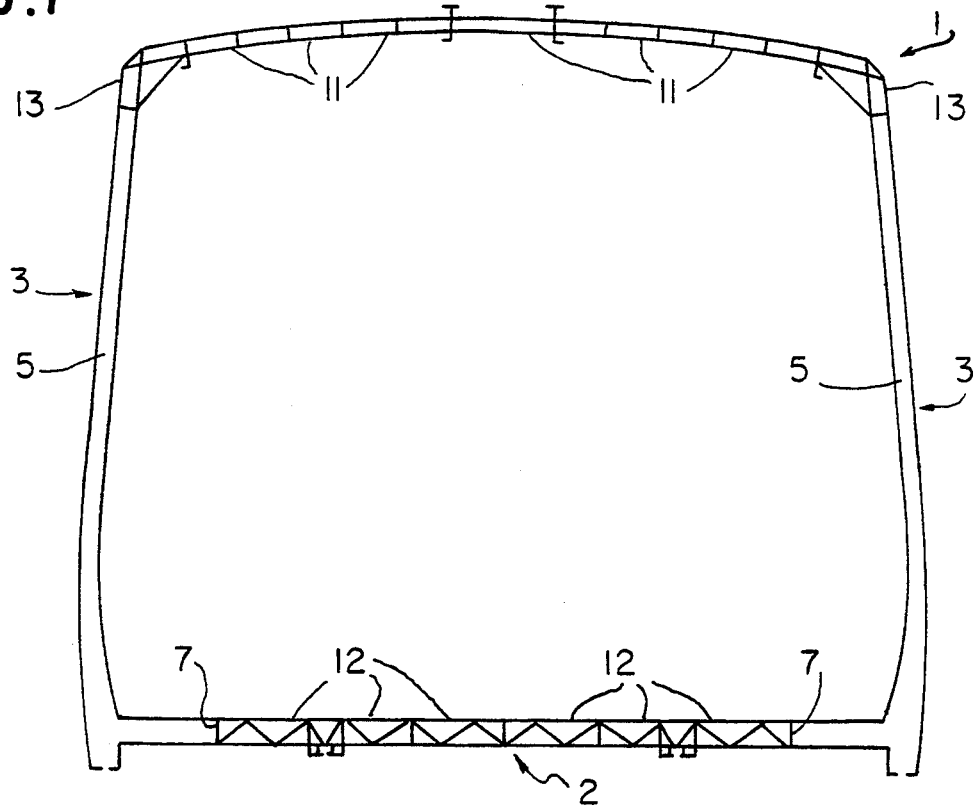
FIG. 7 is a cross section in an enlarged scale along line VII—VII of FIG. 3.
Figure 8:
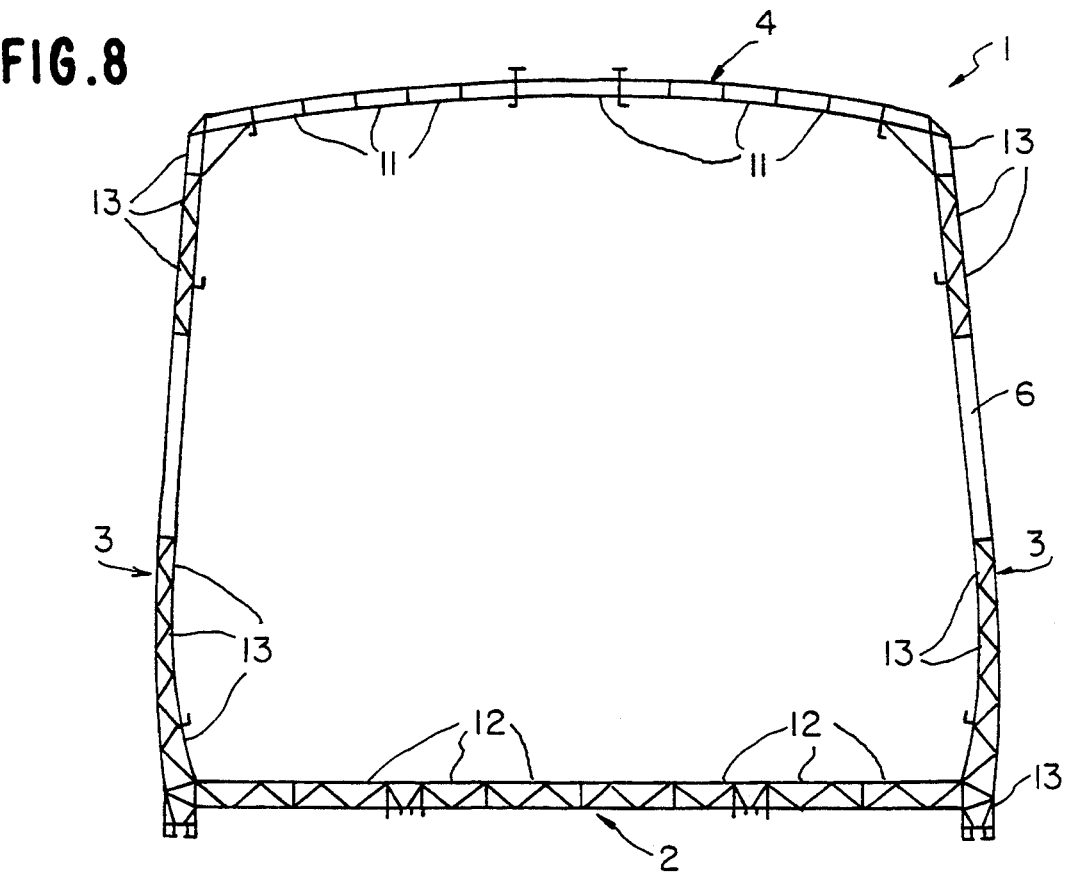
FIG. 8 is a cross section in an enlarged scale along line VIII—VIII of FIG. 3.

Examples of such structural panels are shown in detail in FIG. 4 and in FIGS. 9 through 12: those corresponding to the platform 2 are indicated as 12, those related to the body sides 3 are indicated as 13 and those corresponding to the roof 4 are indicated as 11.

Each of these structural panels essentially comprises (FIG. 10) an inner wall 14 and an outer wall 15, relatively thin and normally flat or slightly bent as a function of the general shape of the corresponding zone of the body, and an intermediate structure 16 having a generally corrugated configuration and placed in the interspace delimited by the two walls 14, 15 for their mutual rigid connection. This substantially corrugated structure 16 is defined by relatively thin baffles 17 arranged according to a generally zigzag configuration, having their respective generating lines parallel to one another and connected along the respective longitudinal edges alternatively to the inner wall 14 and to the outer wall 15.

Figure 9:
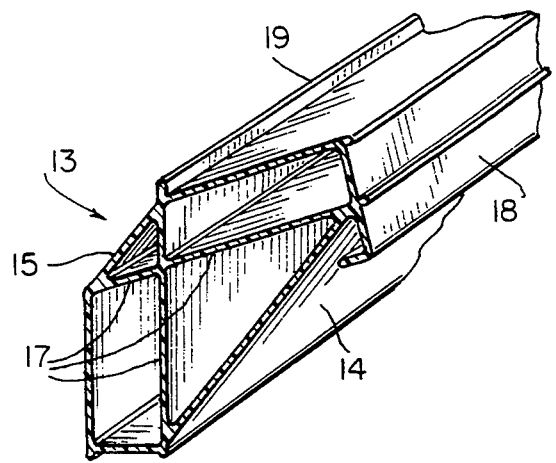
FIG. 9 is fragmentary perspective view in an enlarged scale of the particular indicated by arrow IX in FIG. 4.
Figure 10:
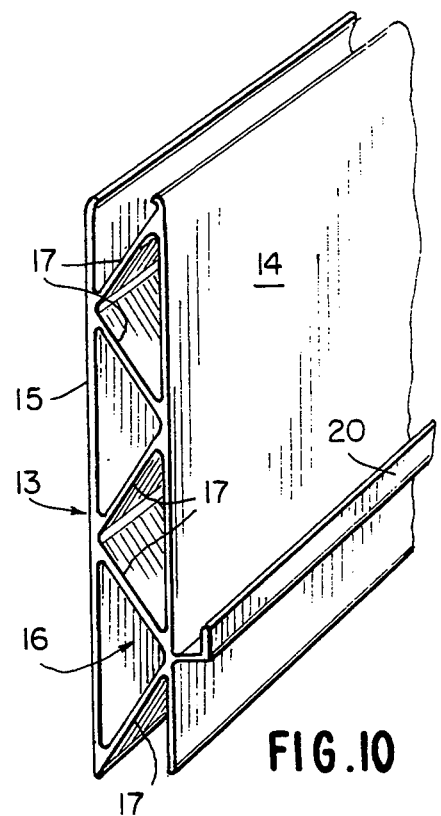
FIG. 10 is a partial, perspective and enlarged view of the particular indicated by arrow X in FIG. 4.
Figure 12:
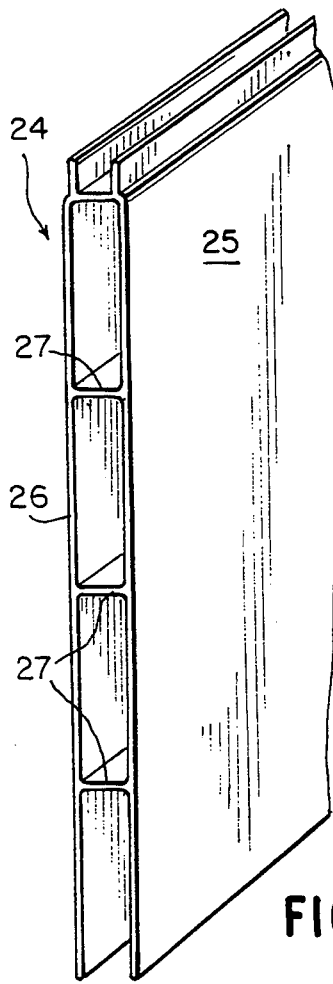
FIG. 12 is a partial, perspective and enlarged view of the particular indicated by arrow XII in FIG. 4.
Figure 11:
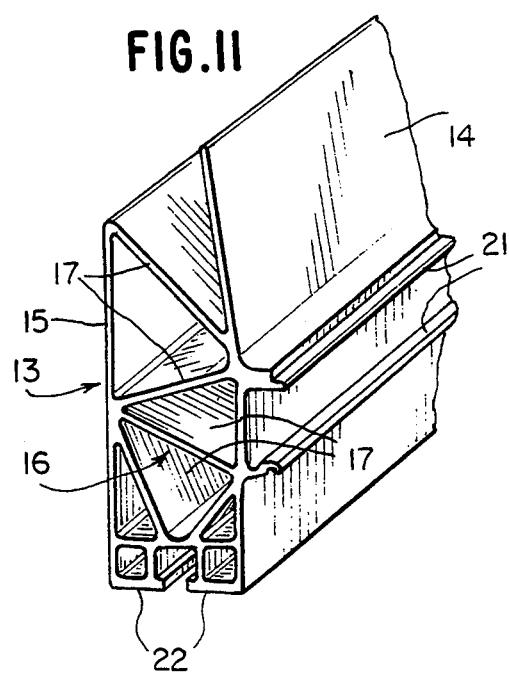
FIG. 11 is a partial, perspective and enlarged view of the particular indicated by arrow XI in FIG. 4.

Moreover some of the structural panels 11-13 are also formed with wings, appendages and projections protruding inwardly and/or outwardly of the body, such as those indicated as 18, 19 in FIG. 9 showing one of the panels 13 connecting between one of the body sides 3 and the roof 4, or that indicated as 20 in FIG. 10 showing one of the intermediate panels 13 of one body side 3, or those indicated as 21 and 22 in FIG. 11, showing one of the panel 13 connecting between one body side 3 and the platform 2.

Preferably each of the structural panels 11, 12 and 13 is metallic, and is formed in a single integral piece by means of extrusion.

As an alternative, such structural panels 11, 12 and 13 can be made by reinforced plastic materials (structural composites), also formed in a single piece by means of poltrusion. The panel 13 in FIG. 9 is shown as being of plastic material by way of example.

According to a further alternative embodiment the intermediate corrugated structures 16 of each panel 11, 12, 13 can be formed by a metal plate or by a sheet of structural plastic composite material, preliminarly corrugated and then rigidly fixed along the crest of the corrugations alternatively to the corresponding walls 14 and 15, by means of welding or glueing.

Figure 2:
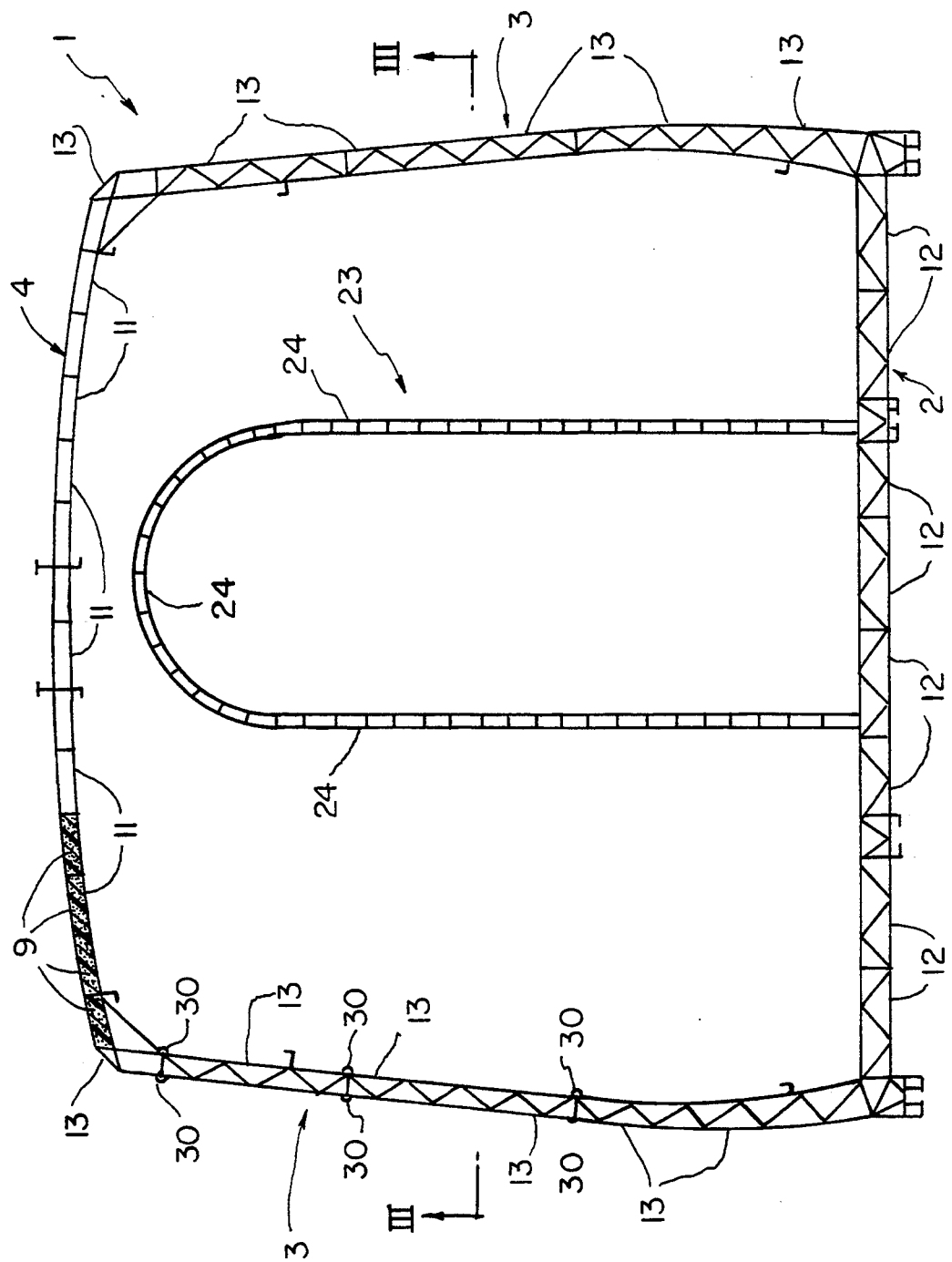
FIG. 2 is a cross section in an enlarged scale along line II—II of FIG. 1.

The interspace of the structural panels 11, 12 and 13 can be conveniently filled with a foamed material, having the function of structural stabilization and thermal insulation and sound proofing. Some of the panels 11 in FIG. 2 are provided with a foamed material 9 by way of example.

As previously clarified the structural panels 11, 12 and 13, thus previously formed or pre-assembled, are rigidly connected to one another along the respective longitudinal edges, conveniently by means of continuous automated solderings or welding, so as to complete the annular series which globally defines the body structure 1. Several representative welds 30 have been schematically shown in FIG. 2.

Such a structure can be further completed by complementary elements (not shown in the drawings) for localized functions and load bearing, such as headstock girders and frameworks, support beams onto the vehicle bogies, support members for the access doors.

Moreover, in the areas corresponding to the openings 8 of the platform 2, stabilizing bulkheads 23 are provided for, which are generally oriented transverse to the longitudinal direction of the body structure 1. The bulkheads 23, together with the headstocks walls (not shown in the drawings since conventional) and with possible further inner walls (also not shown and generally known) act as structural stabilizing members with respect to the operation loads for the tubular body structure. These bulkheads 23 are also constituted (FIGS. 4 and 12) by structural panels 24 also formed by two walls 25, 26 connected to each other by intermediate baffles 27, preferably oriented perpendicularly to the walls 25 and 26.

A similar disposition can be employed, as an alternative to the corrugated inner structure 16 and according to what is shown in the drawings, for the manufacturing of the panels 11 of the roof 4 of the body structure 1.

It will be apparent from the above that the body structure according to the invention can be produced and assembled in a simplified and relatively cheaper way with respect to the conventional structures, is appreciably lighter with respect thereto and enables, for its manufacturing, the use of automated joining equipments. It further provides high rigidity and structural uniformity, with relatively high frequency in the main vibration modes and reduced dispersion in the local vibration modes, and moreover ensures the maximum flexibility and versatility as far as the arrangement of the equipments and fittings of the railway carriage is concerned.

Naturally the details of construction and the embodiments can be widely varied with respect to what has been disclosed and illustrated without thereby departing from the scope of the invention such as defined in the appended claims.

What we claim is:

1. Body structure for railway vehicles, comprising a load bearing body-work defining a platform, body sides and a roof of the body, each constituted by hollow structural panels extending longitudinally and substantially continuously over the entire length of the body, each of said panels having respective longitudinal edges and being solely formed by an inner wall, an outer wall and intermediate longitudinal baffles, said baffles having a substantially corrugated disposition with generating lines parallel to one another, said baffles connecting said inner and outer walls to each other, the longitudinal edges of each structural panel being rigidly connected to the corresponding longitudinal edges of the adjacent structural panels so as to define a tubular body, said body structure further comprising inner transverse structural member connected to the body for stabilising said tubular body.

2. Body structure according to claim 1, wherein each structural panel is formed by a single metallic extruded element.

3. Body structure according to claim 1, wherein each structural panel is formed by a single element of reinforced plastic material.

4. Body structure according to claim 1, comprising a corrugated intermediate sheet whose corrugations define the said baffles, the said corrugations having respective crests joined to the said inner and outer walls of the said panels.

5. Body structure according to claim 1, wherein the said intermediate baffles are substantially flat and disposed according to a zigzag configuration.

6. Body structure according to claim 5, wherein the said intermediate baffles have respective longitudinal edges alternatively fixed to the inner wall and to the outer wall of the respective structural panels.

7. Body structure according to claim 1, wherein the said inner and outer walls of each structural panel define an interspace and the said interspace is filled with a foamed material.

8. Body structure according to claim 1, wherein the structural panels are connected to each another by means of continuous joining means.

* * * * *

UNITED STATES PATENT AND TRADEMARK OFFICE
CERTIFICATE OF CORRECTION

PATENT NO.   : 5,383,406
DATED        : January 24, 1995
INVENTOR(S)  : Pietro Vanolo et al It is certified that error(s) appears in the above-identified patent and that said Letters Patent is hereby corrected as shown below:

On the title page:

In item "[30]" delete "December 29, 1992" and insert --December 30, 1992--.

Signed and Sealed this

Thirteenth Day of June, 1995

Attest:

BRUCE LEHMAN

*Attesting Officer*          *Commissioner of Patents and Trademarks*